US00PP33322P2

(12) United States Plant Patent
Heuger

(10) Patent No.: US PP33,322 P2
(45) Date of Patent: Aug. 3, 2021

(54) ***HELLEBORUS* PLANT NAMED 'COSEH 6100'**

(50) Latin Name: ***Helleborus* x *ericsmithii* X *Helleborus* x *hybridus***
Varietal Denomination: COSEH 6100

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 51 days.

(21) Appl. No.: 16/873,647

(22) Filed: May 27, 2020

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
CPC ..... A01H 5/02; A01H 5/22; A01H 6/72
See application file for complete search history.

*Primary Examiner* — June Hwu
(74) *Attorney, Agent, or Firm* — C. Anne Whealy

(57) ABSTRACT

A new and distinct cultivar of *Helleborus* plant named 'COSEH 6100', characterized by its upright to outwardly spreading and mounded plant habit; moderately vigorous to vigorous growth habit; dark green-colored leaves; freely flowering habit; Purplish red to greyed reddish purple-colored flowers; and good garden performance.

2 Drawing Sheets

Figure 1:
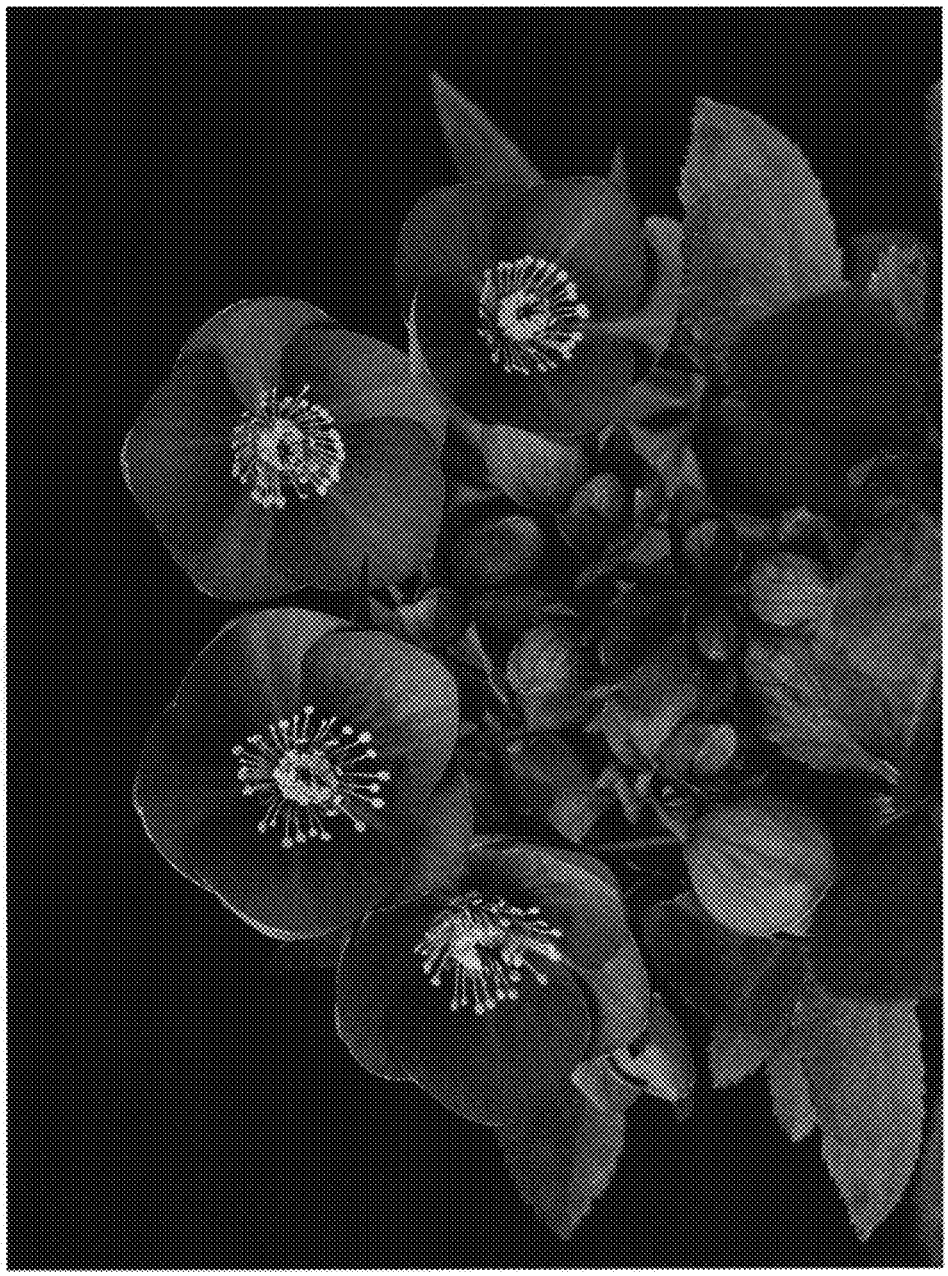

Botanical designation: *Helleborus* x *ericsmithii* X *Helleborus* x *hybridus*.
Cultivar denomination: 'COSEH 6100'.

CROSS-REFERENCED TO CLOSELY-RELATED APPLICATIONS

Title: *Helleborus* Plant Named 'COSEH 6000'
Inventor/Applicant: Josef Heuger
Filed: Concurrently with the instant application (U.S. Plant patent application Ser. No. 16/873,648)
Title: *Helleborus* Plant Named 'COSEH 6300'
Inventor/Applicant: Josef Heuger
Filed: Concurrently with the instant application (U.S. Plant patent application Ser. No. 16/873,646)
Title: *Helleborus* Plant Named 'COSEH 7900'
Inventor/Applicant: Josef Heuger
Filed: Concurrently with the instant application (U.S. Plant patent application Ser. No. 16/873,651)
Title: *Helleborus* Plant Named 'COSEH 8000'
Inventor/Applicant: Josef Heuger
Filed: Concurrently with the instant application (U.S. Plant patent application Ser. No. 16/873,650)

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jun. 6, 2019, application number 2019/1385. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus* x *ericsmithii* X *Helleborus* x *hybridus* and hereinafter referred to by the name 'COSEH 6100'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in December, 2011 of a proprietary selection of *Helleborus* x *ericsmithii* identified as code number P840, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in December, 2013.

Asexual reproduction of the new *Helleborus* plant by in vitro axillary meristem culture in a controlled environment in Glandorf, Germany since March, 2014 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 6100'. These characteristics in combination distinguish 'COSEH 6100' as a new and distinct *Helleborus* plant:

1. Upright to outwardly spreading and mounded plant habit.
2. Moderately vigorous to vigorous growth habit.
3. Dark green-colored leaves.
4. Freely flowering habit.
5. Purplish red to greyed reddish purple-colored flowers.
6. Good garden performance.

Plants of the new *Helleborus* differ from plants of the female parent selection in the following characteristics:

1. Plants of the new *Helleborus* are more compact than and not as vigorous as plants of the female parent selection.
2. Flowers of plants of the new *Helleborus* are lighter greyed purple in color than flowers of plants of the female parent selection.

Plants of the new *Helleborus* differ from plants of the male parent selection in the following characteristics:

1. Plants of the new *Helleborus* are more vigorous than plants of the male parent selection.
2. Plants of the new *Helleborus* flower earlier than plants of the male parent selection.

Plants of the new *Helleborus* can be compared to plants of *Helleborus* x *ericsmithii* X *Helleborus* x *hybridus* 'COSEH 6000', disclosed in a U.S. Plant Patent application filed concurrently. Plants of the new *Helleborus* differ primarily from plants of 'COSEH 6000' in flower color as plants of the new *Helleborus* have greyed purple to greyed red purple-colored flowers whereas plants of 'COSEH 6000' have dark greyed purple-colored flowers.

Plants of the new *Helleborus* can be compared to plants of *Helleborus* x *ericsmithii* X *Helleborus* x *hybridus* 'COSEH 6300', disclosed in a U.S. Plant Patent application filed concurrently. Plants of the new *Helleborus* differ primarily from plants of 'COSEH 6300' in flower color as plants of the new *Helleborus* have greyed purple to greyed red purple-colored flowers whereas plants of 'COSEH 6300' have yellow green to green white-colored flowers with red purple to greyed purple-colored margins.

Plants of the new *Helleborus* can be compared to plants of *Helleborus* x *ericsmithii* X *Helleborus* x *hybridus* 'COSEH 7900', disclosed in a U.S. Plant Patent application filed concurrently. Plants of the new *Helleborus* differ primarily from plants of 'COSEH 7900' in flower color as plants of the new *Helleborus* have greyed purple to greyed red purple-colored flowers whereas plants of 'COSEH 7900' have greyed purple-colored flowers.

Plants of the new *Helleborus* can be compared to plants of *Helleborus* x *ericsmithii* X *Helleborus* x *hybridus* 'COSEH 8000', disclosed in a U.S. Plant Patent application filed concurrently. Plants of the new *Helleborus* differ primarily from plants of 'COSEH 8000' in flower color as plants of the new *Helleborus* have greyed purple to greyed red purple-colored flowers whereas plants of 'COSEH 8000' have greyed purple to dark purple-colored flowers.

Plants of the new *Helleborus* can also be compared to plants of *Helleborus* x *ericsmithii* X *Helleborus* x *hybridus* 'LEM 100', disclosed in U.S. Plant Pat. No. 25,646. In side-by-side comparisons, plants of the new *Helleborus* differ primarily from plants of 'LEM 100' in the following characteristics:

1. Plants of the new *Helleborus* are more vigorous than plants of 'LEM 100'.
2. Plants of the new *Helleborus* have smaller flowers than plants of 'LEM 100'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 6100' grown in a container.

Figure 2:
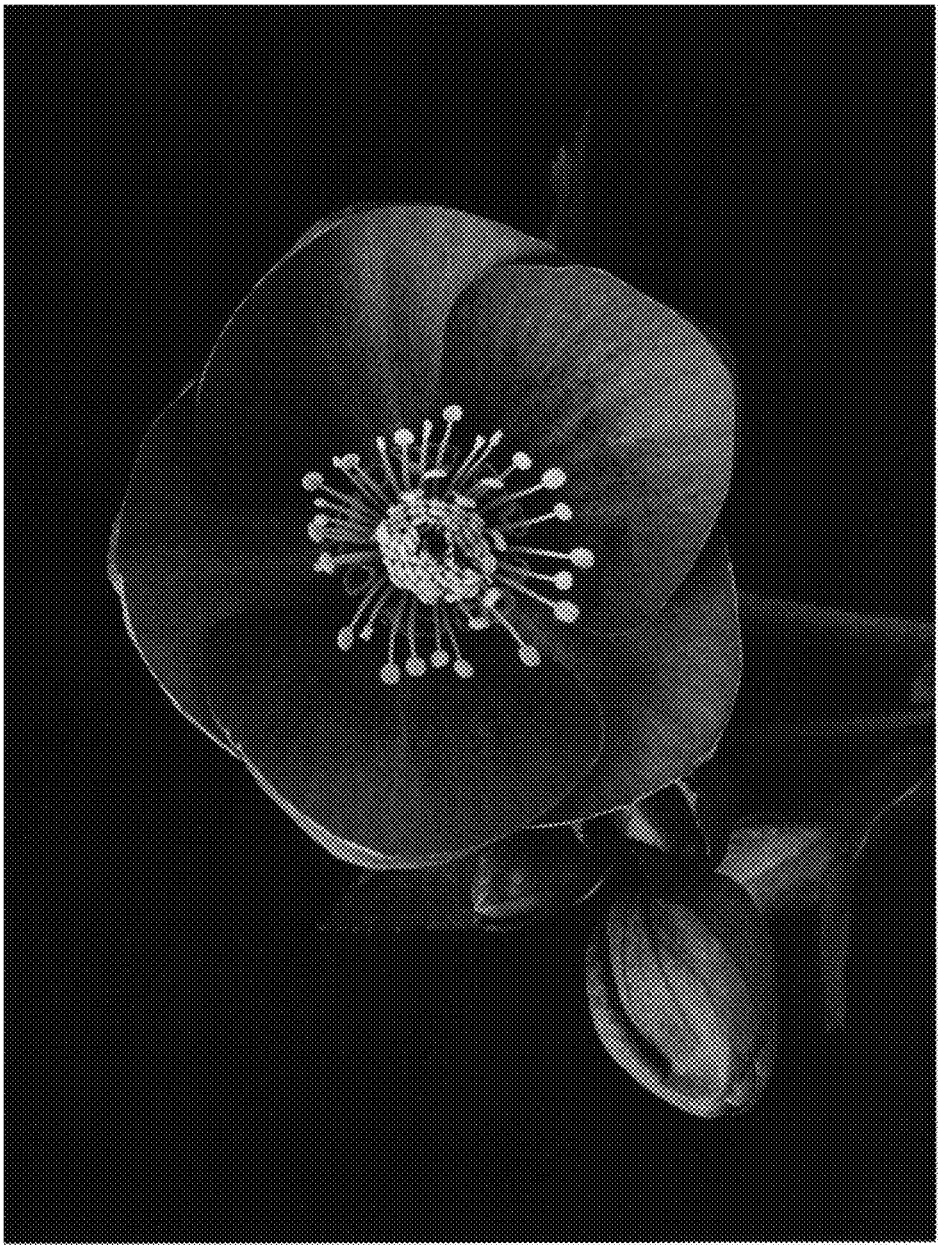

The photograph on the second sheet (FIG. 2 of 2) is a close-up view of typical flowers and flower buds of 'COSEH 6100'.

DETAILED BOTANICAL DESCRIPTION

The aforementioned photographs and following observations, measurements and values describe plants grown during December in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were four months old when the photographs and the description were taken. In the following description, color references are made to The Royal Horticultural Society Colour Chart, 2015 Edition, except where general terms of ordinary dictionary significance are used.

Botanical classification: *Helleborus* x *ericsmithii* X *Helleborus* x *hybridus* 'COSEH 6100'.

Parentage:

*Female, or seed, parent.*—Proprietary selection of *Helleborus* x *ericsmithii* disclosed as code number P840, not patented.

*Male, or pollen, parent.*—Unnamed selection of *Helleborus* x *hybridus*, not patented.

Propagation:

*Type.*—In vitro axillary meristem culture.

*Time to initiate roots, winter.*—About 55 days at temperatures about 12° C.

*Time to produce a rooted young plant, winter.*—About 170 days at temperatures ranging from 4° C. to 15° C.

*Root description.*—Thick to thin, fleshy; typically white to brown in color, actual color of the roots is dependent on substrate composition, water quality, fertilizer type and formulation, substrate temperature and physiological age of roots.

*Rooting habit.*—Low branching; sparse.

Plant description:

*Plant and growth habit.*—Herbaceous perennial; upright and mounding plant habit with flowers held within and above the foliar plane; plant shape, roughly flattened globular; moderately vigorous to vigorous growth habit and moderate to rapid growth rate.

*Plant height, soil level to top of foliar plane.*—About 22.7 cm.

*Plant height, soil level to top of flowers.*—About 40.2 cm.

*Plant diameter (area of spread).*—About 58 cm.

Leaf description:

*Arrangement*.—Leaves arranged in a basal rosette; leaves palmately compound with typically five leaflets per leaf.

*Leaf length*.—About 16 cm.

*Leaf width*.—About 16.9 cm.

*Leaflet length*.—About 10.1 cm.

*Leaflet width*.—About 5.1 cm.

*Leaf shape*.—Palmate; reniform to orbicular in outline.

*Leaflet shape*.—Elliptic to ovate or obovate.

*Leaflet apex*.—Acute.

*Leaflet base*.—Attenuate.

*Leaflet margin*.—Serrate; coarsely undulate.

*Leaflet texture and luster, upper surface*.—Smooth, glabrous; leathery; slightly glossy.

*Leaflet texture and luster, lower surface*.—Smooth, glabrous; leathery; matte.

*Leaflet venation pattern*.—Pinnate.

*Leaflet color*.—Developing leaflets, upper surface: Close to 137A; midvein proximally, close to 185A. Developing leaflets, lower surface: Close to 197A; midvein, close to 185A. Fully developed leaflets, upper surface: Slightly darker than between NN137A and 147A; venation, close to 144A. Fully developed leaflets, lower surface: Close to 147B; venation, close to 187A.

*Petioles*.—Length: About 17.5 cm. Diameter: About 6 mm to 6.5 mm. Strength: Strong. Texture and luster, upper and lower surfaces: Smooth, glabrous; slightly to moderately glossy. Color, upper and lower surfaces: Close to 150D heavily covered with fine dots, close to 187A to 187B.

Flower description:

*Flower shape and habit*.—Rotate flowers; flowers moderately cupped; arranged in panicles; freely flowering habit with about twelve flowers per inflorescence and about 96 flowers developing per plant; flowers face mostly outwardly to slightly nodding.

*Fragrance*.—None detected.

*Natural flowering season*.—Plants begin flowering about ten months after planting; plants flower naturally from winter into the late winter in Germany.

*Flower longevity on the plant*.—About ten days; sepals persistent, other flower parts are not persistent.

*Flower buds*.—Length: About 1.8 cm. Diameter: About 1.1 cm. Shape: Ovate. Texture and luster: Smooth, glabrous; matte. Color: Close to 145D strongly tinged with close to N187D; towards the base and venation, close to 187B.

*Inflorescence height* (*including peduncle*).—About 44.9 cm.

*Inflorescence diameter*.—About 22.1 cm.

*Flower diameter*.—About 5.7 cm by 5.7 cm.

*Flower depth* (*height*).—About 2.7 cm.

*Petals*.—All petals are transformed into nectaries.

*Sepals*.—Quantity and arrangement: About five, arranged in a single whorl. Length: About 3.5 cm. Width: About 3.4 cm. Shape: Broadly ovate, moderately concave. Apex: Obtuse. Base: Truncate to broadly cuneate. Margin: Entire; not undulate. Texture and luster, upper and lower surfaces: Smooth, glabrous; matte. Color: When opening, upper surface: Close to 145C to 145D towards the margins and apex, close to 186C; venation, similar to lamina. When opening, lower surface: Close to between N187B and 201A; venation, close to 187A. Fully opened, upper surface: Close to 185C; center, tinged with close to 145C; towards the base, close to 145D; with development, color becoming closer to N77C slightly tinged towards the center with 148C and proximally, fine dots, close to 187B; venation, similar to lamina. Fully opened, lower surface: Close to 185C; center, slightly tinged with close to 201A; with development, color becoming closer to N186B and venation, close to N186C.

*Flower bracts*.—Quantity per flower: Typically one or two. Length: About 5.8 cm. Width: About 3.5 cm. Shape: Ovate, occasionally cleft or tri-lobed. Apex: Acute. Base: Truncate. Margin: Finely serrate; slightly undulate. Color, upper surface: Close to NN137D; midvein, close to 183C. Color, lower surface: Close to between 147B and 191A; venation, close to N186C.

*Peduncles*.—Length: About 38.9 cm. Diameter: About 8.5 mm to 10 mm. Aspect: About 15° from vertical. Strength: Strong. Texture and luster: Smooth, glabrous; moderately glossy. Color: Close to 150D, heavily covered with fine dots, close to 187A.

*Pedicels*.—Length: About 2.3 cm. Diameter: About 2 mm to 3 mm. Aspect: About 10° to 30° from peduncle axis. Strength: Moderately strong. Texture and luster: Smooth, glabrous; moderately glossy. Color: Close to N148D; moderately covered with fine dots, close to 187D.

*Reproductive organs*.—Stamens: Quantity per flower: About 60. Filament length: About 1.3 cm. Filament color: Close to between 150D and 155C. Anther shape: Double and broadly reniform; basifixed. Anther size: About 1.5 mm by 2 mm. Anther color: Close to 150C. Pollen amount: Moderate to abundant. Pollen color: Close to 4D to lighter than 4D. Pistils: Quantity per flower: About five to nine. Pistil length: About 1 cm. Stigma diameter: About 0.3 mm. Stigma shape: Club-shaped. Stigma color: Close to 155A. Style length: About 9 mm. Style color: Close to 184B. Ovary color: Close to 157C; ribs, close to 184C. Nectaries (transformed petals): Quantity per flower: About 13. Length: About 1.1 cm. Diameter: About 4 mm. Shape: Tubular, flattened. Texture and luster, inner and outer surfaces: Smooth, glabrous; slightly glossy. Color, immature, inner surface: Close to 145A; distally, close to 150B. Color, immature, outer surface: Close to 145A; distally, close to 150B; spot at base, close to 144B. Color, mature, inner surface: Close to N144B; distally, close to 151B; with development, distally becoming closer to 153D; venation, similar to lamina. Color, mature, outer surface: Close to N144B; distally, close to 151B; spot at base, close to 146C to 146D; with development, distally becoming closer to 153D and spot, closer to 146D; venation, similar to lamina.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 6100' as illustrated and described.

* * * * *